United States Patent [19]

Lindstrom

[11] Patent Number: 4,711,638
[45] Date of Patent: Dec. 8, 1987

[54] INTRAOCULAR LENS

[76] Inventor: Richard L. Lindstrom, 1065 W. Ferndale Rd., Wayzata, Minn. 55391

[21] Appl. No.: 861,707
[22] Filed: May 12, 1986
[51] Int. Cl.$^4$ .................... A61F 2/16; A61B 17/00
[52] U.S. Cl. .................................. 623/6; 128/303 R
[58] Field of Search ........................ 623/6; 128/303 R

[56] References Cited

U.S. PATENT DOCUMENTS

| 4,316,293 | 2/1982 | Bayers | 623/6 |
| 4,363,143 | 12/1982 | Callahan | 623/6 |
| 4,463,458 | 8/1984 | Seidner | 623/6 |
| 4,477,931 | 10/1984 | Kelman | 623/6 |
| 4,494,254 | 1/1985 | Lopez | 623/6 |
| 4,600,003 | 7/1986 | Lopez | 128/303 R |

FOREIGN PATENT DOCUMENTS 1103399  5/1955  France ................................ 623/6

OTHER PUBLICATIONS

Model PC-80 Posterior Chamber (Knolle) American Medical Optics (phamplet) 4 pages, Sep. 1982.
Lester Posterior Chamber Lens (advertisement brochure), 2 pages Intermedics Intraocular Inc., Aug. 1982.

*Primary Examiner*—Ronald L. Frinks
*Attorney, Agent, or Firm*—Hugh D. Jaeger

[57] ABSTRACT

Intraocular lens including a lens optic having two haptic loops secured substantially adjacent to each other near a common point of the lens optic, and extending about the lens optic to a position opposing the common point of securement about the lens optic. The haptic loops can include notches and positioning holes and the optics can include positioning holes. The mirror image haptic loops assume geometrical haptic configurations of circular segments substantially conforming equidistantly about the circumference of the lens, a two straight sided configuration with a connecting outwardly curved circular segment, a two straight sided configuration with a connecting inwardly curved circular segment, two circular segments with a connecting inverted circular segment, or three circular segments with two connecting inverted circular segments. The lens optics can be plano-convex, bi-convex, meniscus or other like optic configurations, including reversed optics. The lenses can be lathe cut or injection molded. The haptic loops can also be angled forward or planar. An insertion slide is included for assisting in inserting a lens into the eye.

5 Claims, 17 Drawing Figures

INTRAOCULAR LENS

CROSS REFERENCES TO CO-PENDING APPLICATIONS

None.

BACKGROUND OF THE INVENTION

1. Field of the Invention

The present invention pertains to an intraocular lens ("IOL") and, more particularly, pertains to an intraocular lens with symmetrical, double-opposing, compressible, cantilevered haptic loops. The IOL can be used in endocapsular and other IOL surgeries.

2. Description of the Prior Art

Endocapsular surgery has been recently recognized in the European medical community as one preference for IOL implants. Prior art lenses have not readily lent themselves to endocapsular surgery.

Lopez, U.S. Pat. No. 4,494,254 illustrates an intraocular lens structure with specially configured loops.

The present invention provides an intraocular lens for endocapsular surgery.

SUMMARY OF THE INVENTION

The general purpose of the present invention is to provide an intraocular lens for endocapsular surgery or in the Bag implantation.

According to one embodiment of the present invention, there is provided an intraocular lens with an optic and symmetrical, double-opposing, compressible, cantilevered haptic loops affixed about a common point of a lens optic. The haptic loops extend therefrom outwardly and then about the circumference of the lens toward an opposing point near the bottom. The haptic loops can either assume geometrical configurations of semi-circular, two straight sections with a middle curvature section, or two or more curvature sections with inverse curvature sections. The loops can also include notches in the haptic loops and positioning keyhole geometry at the ends of the haptic loops.

The lens can be of polymethylmethacrylate ("PMMA"), polysulfone, silicone or hydrogel. The lens can also be lathe cut or injection molded with the haptic loops attached accordingly.

An insertion slide with channeled grooves positions the haptic loops during insertion. The insertion slide includes end forceps tabs, which can assist positioning of the insertion slide during the implant procedure.

One significant aspect and feature of the present invention is an intraocular lens for endocapsular surgery. The lens is of such structure that the haptic loops compress to substantially the size of the optic to lend itself during compressibility for implantation in endocapsular surgery. The haptic loops expand symmetrically to the full size of the capsular bag or the cillary sculus with substantially 360° of support.

Another significant aspect and feature of the present invention is an intraocular lens where the haptic loops expand symmetrically into the containing shape.

Having thus described embodiments of the present invention, it is a principal object hereof to provide an intraocular lens for endocapsular surgery and IOL surgery in general.

DESCRIPTION OF THE PREFERRED EMBODIMENTS

Figure 1:
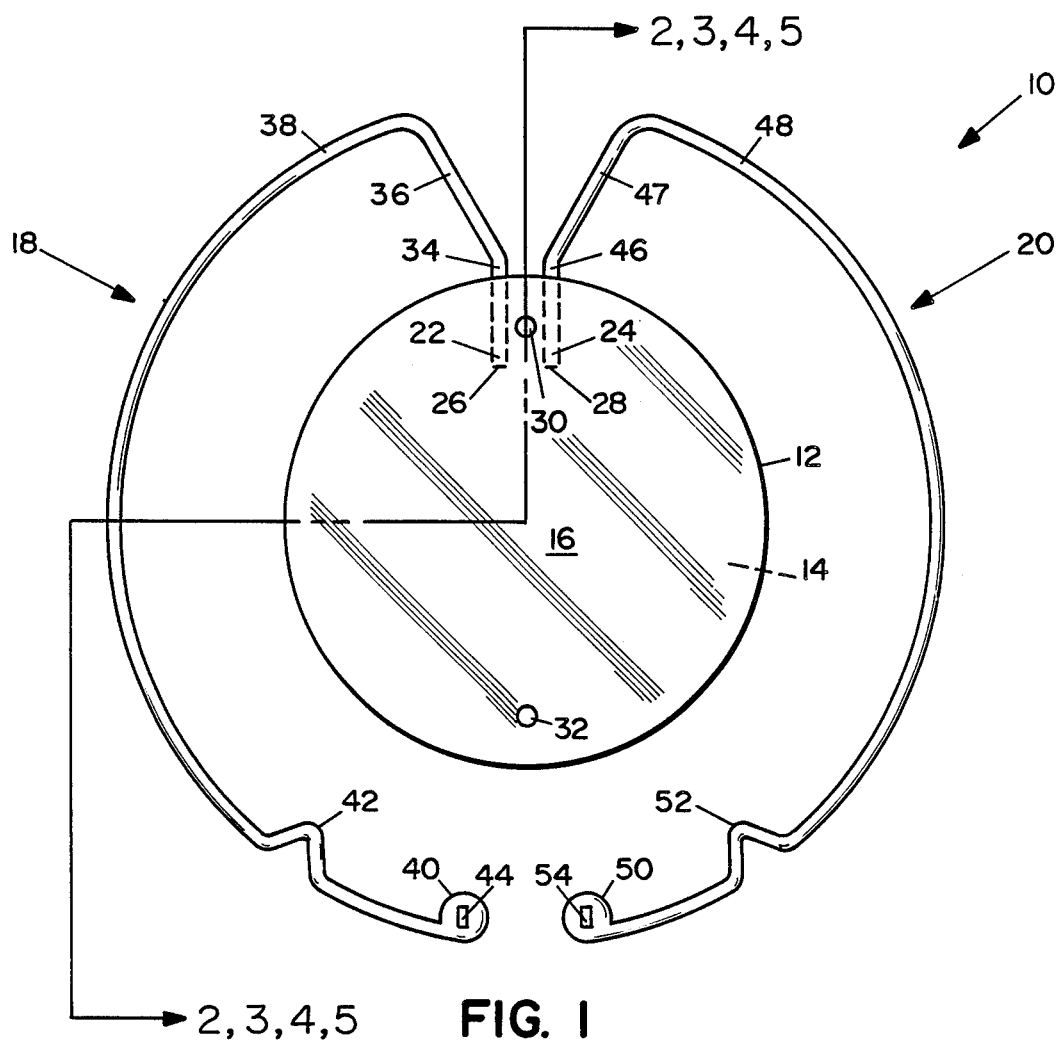
FIG. 1 illustrates a top view of an intraocular lens ("IOL") for endocapsular surgery.

FIG. 1 illustrates a top view of an intraocular lens 10, the present invention, for endocapsular surgery or like IOL surgery including a lens optic 12. The optic 12 includes a planar surface 14 and a convex surface 16. Haptic loops 18 and 20 having ends 22 and 24 secure into holes 26 and 28 in the optic 12, respectively, by known processes. Each of the haptic loops 18 and 20 are symmetrical and opposing, compressible and cantilevered, substantially adjacent to each other near a edge reference point of the optic 12 and adjacent to a positioning hole 30. Loop haptic 18 includes an outwardly extending straight section 34, an angled section 36, and then a circumferencing section 38 about the circumference of the lens optic in an equal radial circumference to that of the lens optic 12. An end 40 of the haptic loop 18 is substantially in line with that end 22. A notch 42 for positioning the lens 10 can be provided in the haptic loop, as well as a geometrical positioning keyhole 44 in the end of the haptic loop 18. Likewise, the loop 20 includes the straight section 46, angled section 47, circular section 48, end 50, notch 52 and geometrical keyhole 54. The lens optic 12 is illustrated as plano-convex in FIGS. 2 and 3, and can also be convex-plano, meniscus of FIG. 4, meniscus-reversed or bi-convex of FIG. 5. The lens optic can be of PMMA, polysulfone, silicone, hydrogel, or other suitable material. The loops can be of PMMA, prolene or other like material. The lens can be injection molded or lathe cut, as also illustrated in FIG. 6. The notches 42 and 52 can be provided as an option in the haptic loops and, likewise, the rectangular keyholes can also be of any suitable geometrical keyhole structure in the end of the loop. While the ends 40 and 50 of the haptic loops 18 and 20 have been rounded, the ends can also be traditional in being a rounded end of the loop without the geometrical keyhole structure. The angle between the straight sections 34 and 36 can be in a range of 0°, as in FIG. 6, to an outwardly extending angle of 75°. The two ends 40 and 50 are positioned near and about a lower positioning hole 32.

Figure 2:
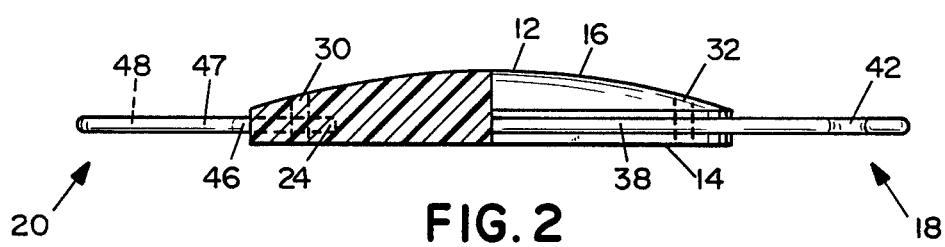
FIG. 2 illustrates a view taken along line 2—2 of FIG. 1 where the haptic loops are planar.

FIG. 2 illustrated a view taken along 2—2 of FIG. 1 where all numerals correspond to those elements previously described. The haptic loops are illustrated as being planar with respect to the plane of the lens optic.

Figure 3:
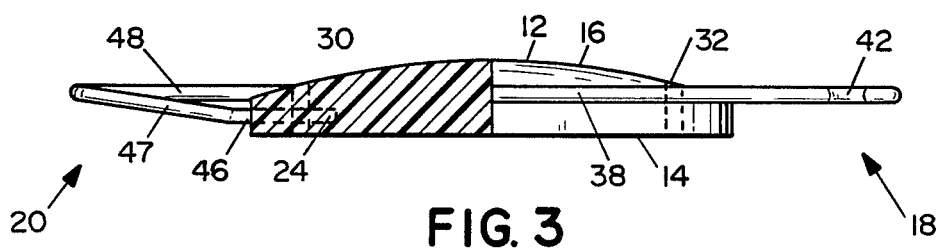
FIG. 3 illustrates a view taken along line 3—3 of FIG. 1 where the haptic loops are angled forward.

FIG. 3 illustrates a view taken along line 3—3 of FIG. 1 where the haptic loops are angled forward in a range of 0 to 10 degrees or preferably in a range of 5 to 10 degrees with respect to the plane of the lens optic.

Figure 4:
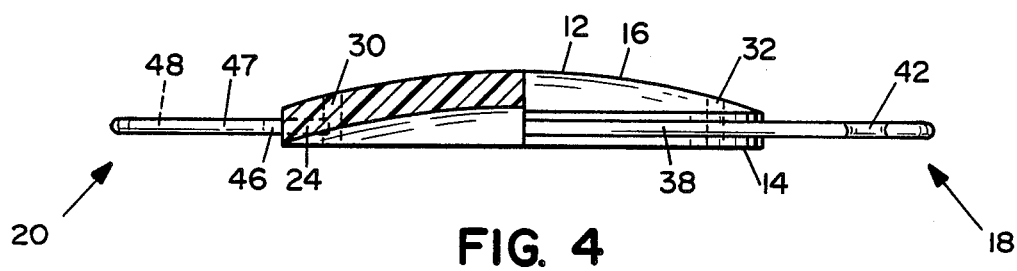
FIG. 4 illustrates a view taken along line 4—4 of FIG. 1 where lens optic in the alternative can be meniscus.

FIG. 4 illustrates a view taken along line 4—4 of FIG. 1 which illustrates the lens optic as being meniscus.

Figure 5:
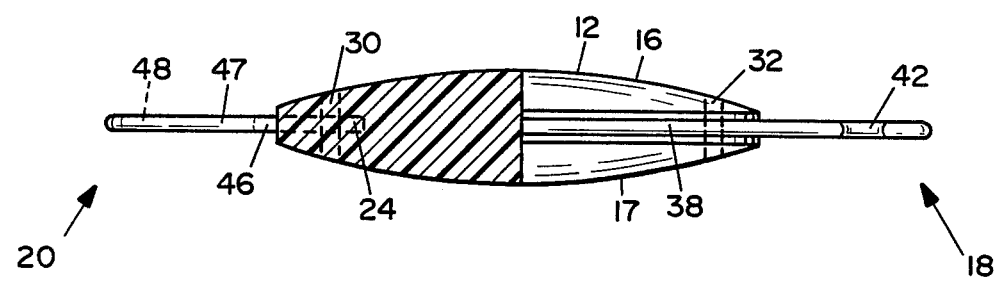
FIG. 5 illustrates a view taken along line 5—5 of FIG. 1 where the lens optic in the alternative can be bi-convex.
Figure 6:
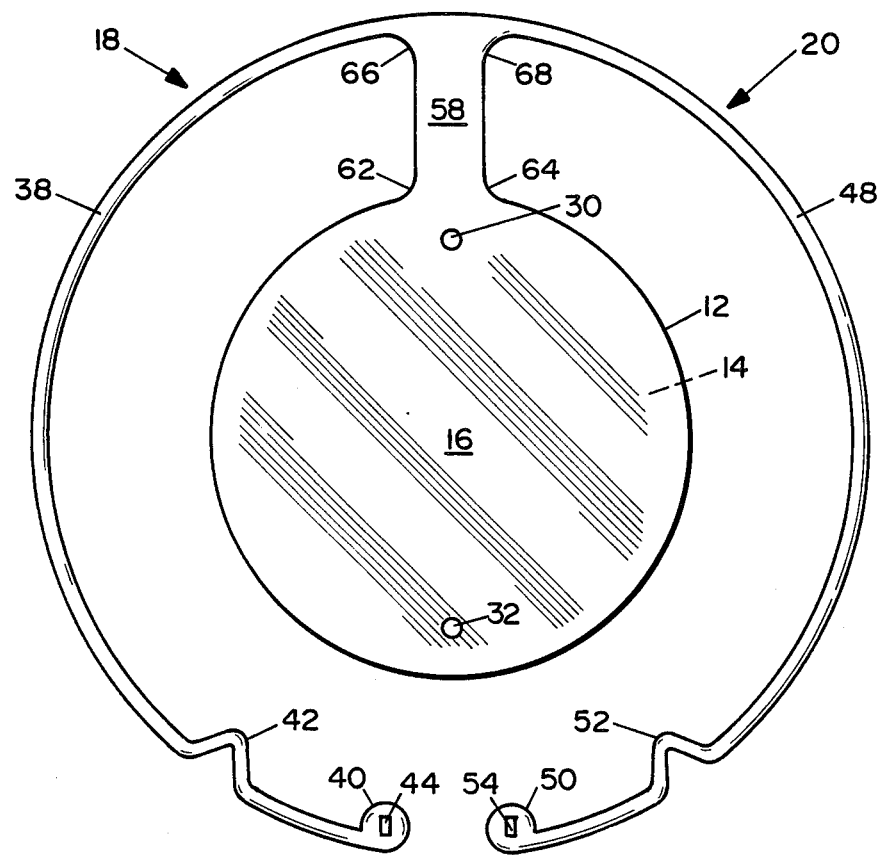
FIG. 6 illustrates a top view of another embodiment of a lathe cut lens where the loops extend from a rectangular member before circumferencing the edge of the lens.

FIG. 5 illustrates a view taken along line 5—5 of FIG. 1 where the lens optic is illustrated as being biconvex, including an opposing convex surface.

FIG. 6 illustrates an alternative embodiment of FIG. 1 where the haptic loops 18 and 20 are lathe cut from the same like material of the lens optic 12 and are contiguous to the lens optic 12. The haptic loops 18 and 20 extend outwardly from rectangular like extending member 58 and circumferencially around the optic 12. Rectangular like member 58, contiguous to haptics 18 and 20 and lens optic 12 dies into the optic 12 at curved areas 62 and 64 and the haptics 18 and 20 at curved areas 66 and 68.

Figure 7:
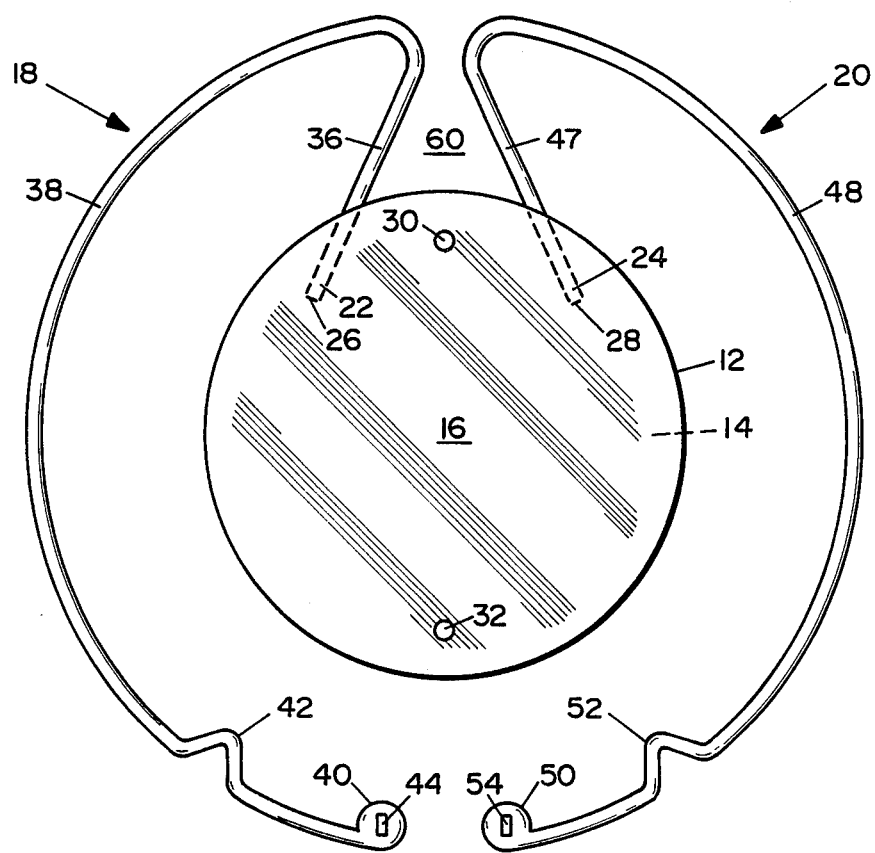
FIG. 7 illustrates a further embodiment where the haptic loops extend inwardly toward each other before circumferencing the edge of the lens.

FIG. 7 illustrates a top view of an additional embodiment of the lens 10 where the portions 36 and 47 of the haptic loops 18 and 20 extend substantially inwardly toward each other at an angle of 0° to an inwardly inclined angle of 75°. Of course, the haptic ends 22 and 24 are positioned in the lens optic as illustrated. A space 60 is provided by the outward angling of the haptic sections 36 and 40.

Figure 8:
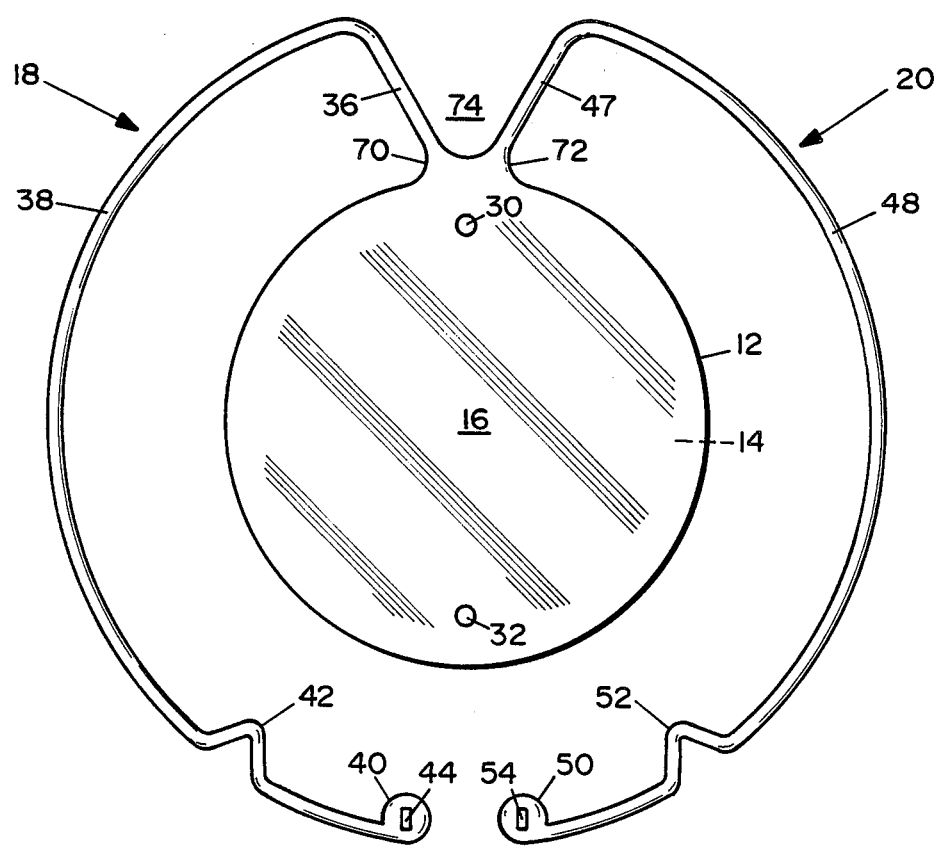
FIG. 8 illustrates a top view of an additional embodiment of a lathe cut IOL.

FIG. 8 illustrates a top view of a lathe cut intraocular lens in the alternative of FIG. 1 where the haptic loops 18 and 20 are lathe cut from the same like material of the lens optic. The haptic loops 18 and 20 extend from a portion of the lens adjacent to positioning hole 30 and are contiguous to the lens optic. Of course, there are no need for loop holes, and likewise, there are no ends of haptic loops secured within holes adjacent to positioning hole 30. The haptic portions 36 and 47 of haptics 18 and 20 are contiguous to and die into the optic 12 at curved areas 70 and 72, respectively, and form space 74. The straight sections of the haptic loops can be angled outwardly as illustrated, extend parallel and straight out perpendicular to the tangent of the lens edge, or angle inwardly accordingly as previously discussed. All other numerals correspond to those elements previously described.

Figure 9:
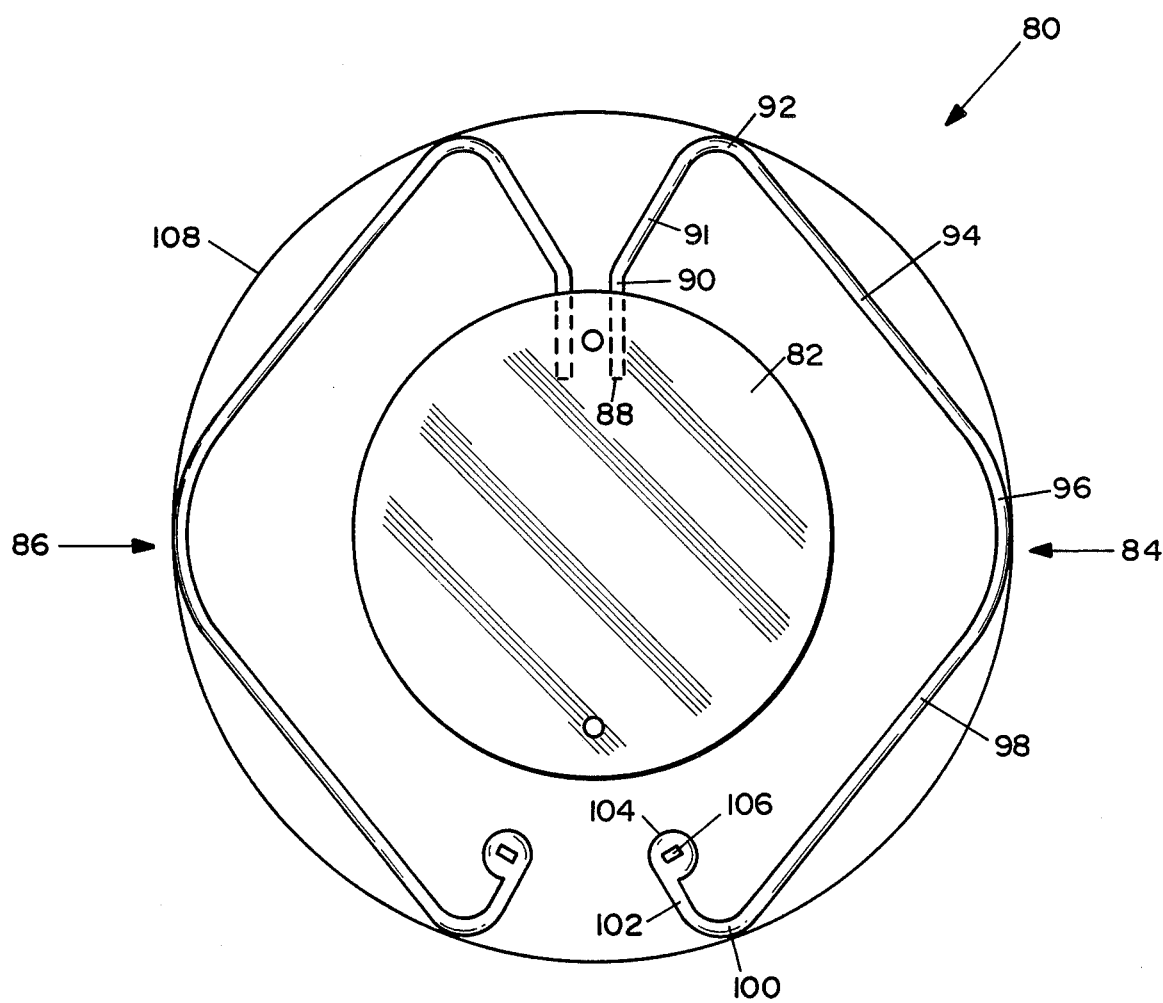
FIG. 9 illustrates a top view of a lens with sections of straight haptic loops connected by a connecting circular segment.

FIG. 9 illustrates a top view of an alternative embodiment of an intraocular lens 80 including haptic loops with two straight sections and one outwardly connecting curved segment. The lens 80 includes an optic 82, and symmetrical double opposing compressible cantilevered haptic loops 84 and 86. Each haptic loop includes an end section 88, short straight section 90, an angled straight section 91, a curved segment 92, first long straight segment 94, an outwardly curved segment 96, second long straight segment 98, curved segment 100, a short straight segment 102, a rounded end 104, and a geometrical keyhole 106. The other haptic loop 86 is identical to the haptic loop 84. The lens 80 is shown with the haptic loops 84 and 86 engaged within the capsular bag 108.

Figure 10:
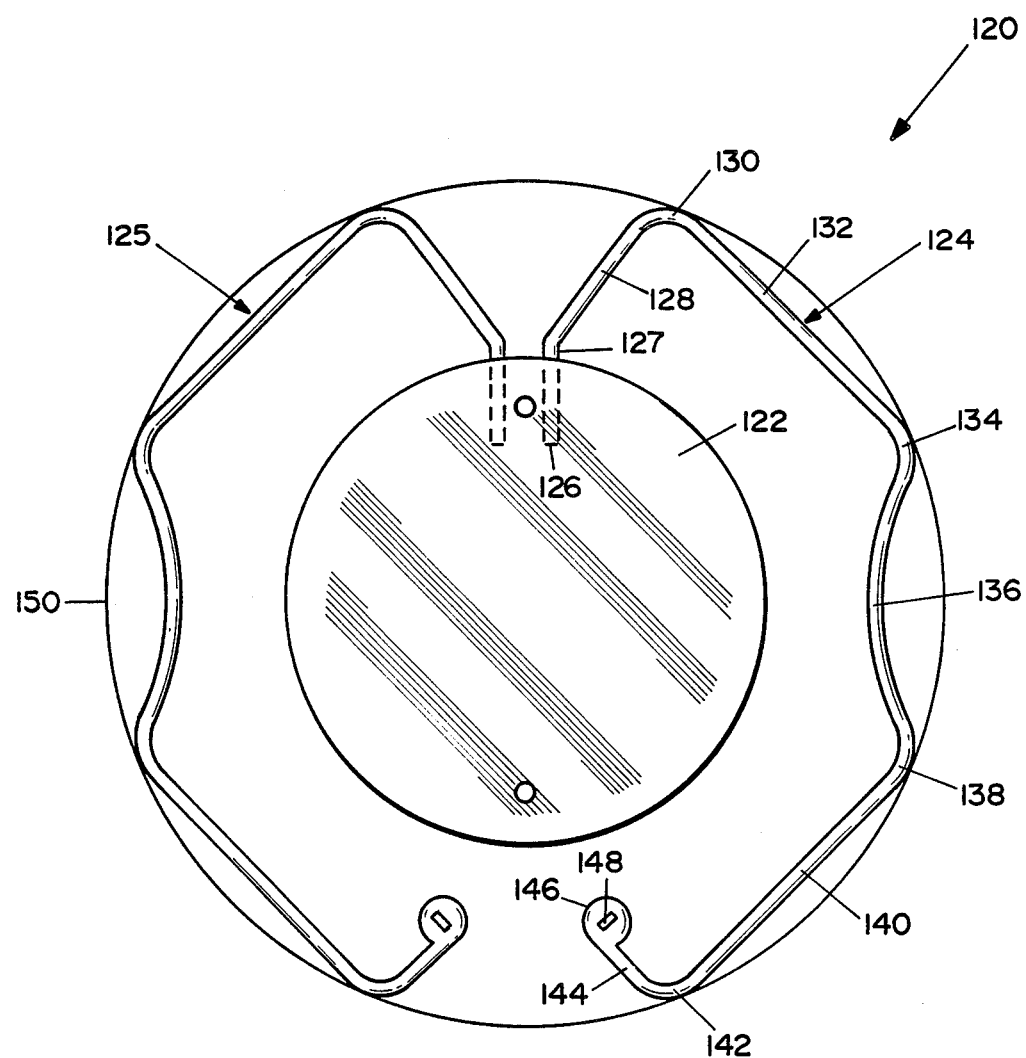
FIG. 10 illustrates a top view of a lens of haptic loops with straight sections connected by an inwardly curved segment.

FIG. 10 illustrates a top view of another embodiment of an intraocular lens 120 similar to that of FIG. 9 except that the center curved segment 136 is inwardly curved rather than outwardly curved as segment 96 in FIG. 9. The lens 120 includes a lens optic 122 and haptic loops 124 and 126. The haptic loops are symmetrical, double-opposing, compressible and cantilevered as previously described, and include an end section 126, a short straight section 127, an angled straight segment 128, a curved segment 130, straight segment 132, curved segment 134, an inwardly curved segment 136, curved segment 138, straight segment 140, curved segment 142, straight segment 144, and a rounded end 146 including a geometrical keyhole 148. The lens 120 is shown with the haptic loops 124 and 126 engaged within the capsular bag 150.

Figure 11:
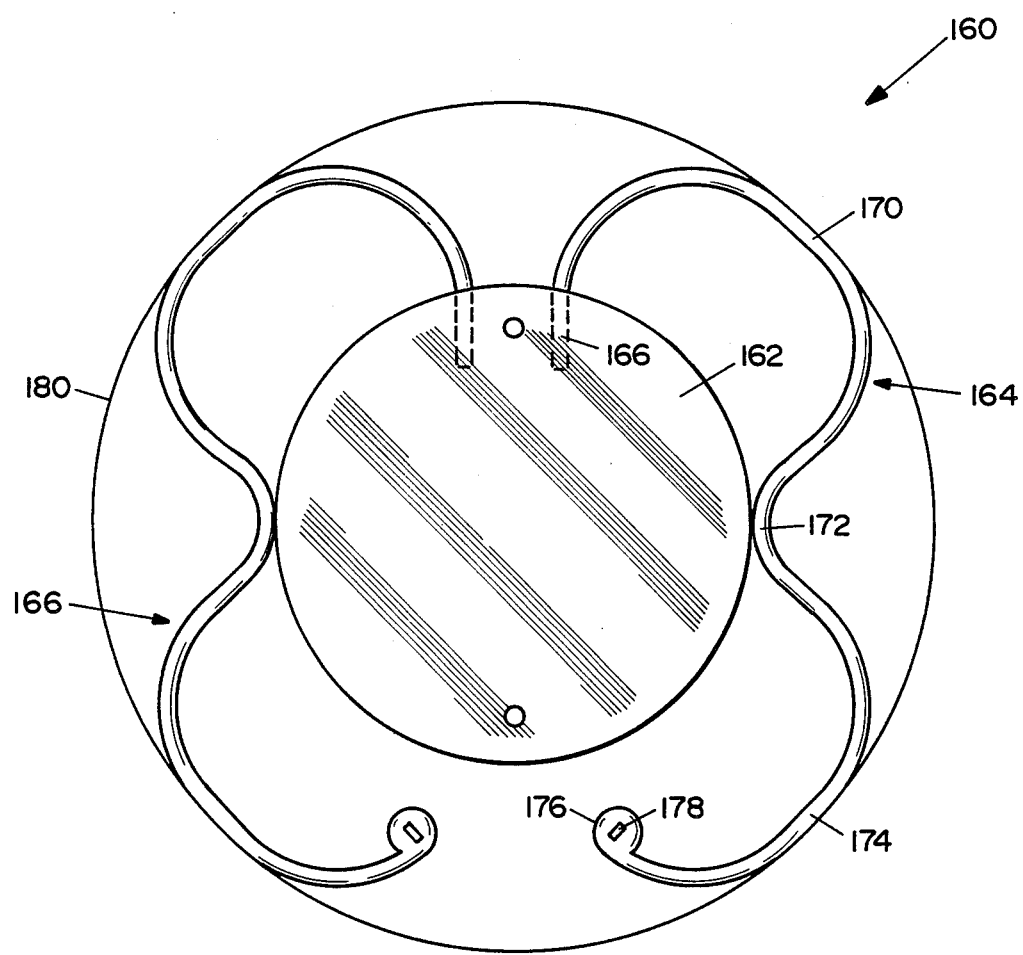
FIG. 11 illustrates a top view of a lens with haptic loops each with two curved segments connected by one inwardly curved segment.

FIG. 11 illustrates a top view of a lens 160 including a lens optic 162 and haptic loops 164 and 166. Haptic loop 164, which is identical and symmetrical to 166, includes end 168, a first outwardly curved segment 170, an inwardly curved segment 172, a second outwardly curved segment 174, and a rounded end 176 which includes a geometric keyhole 178. Haptic loop 166 is a symmetrical opposing mirror image of haptic loop 164. The two haptics 164 and 166 provide for four-point or four-area fixation within the capsular bag 180. The lens 160 is shown with the haptic loops 164 and 166 engaged within the capsular bag 180.

Figure 12:
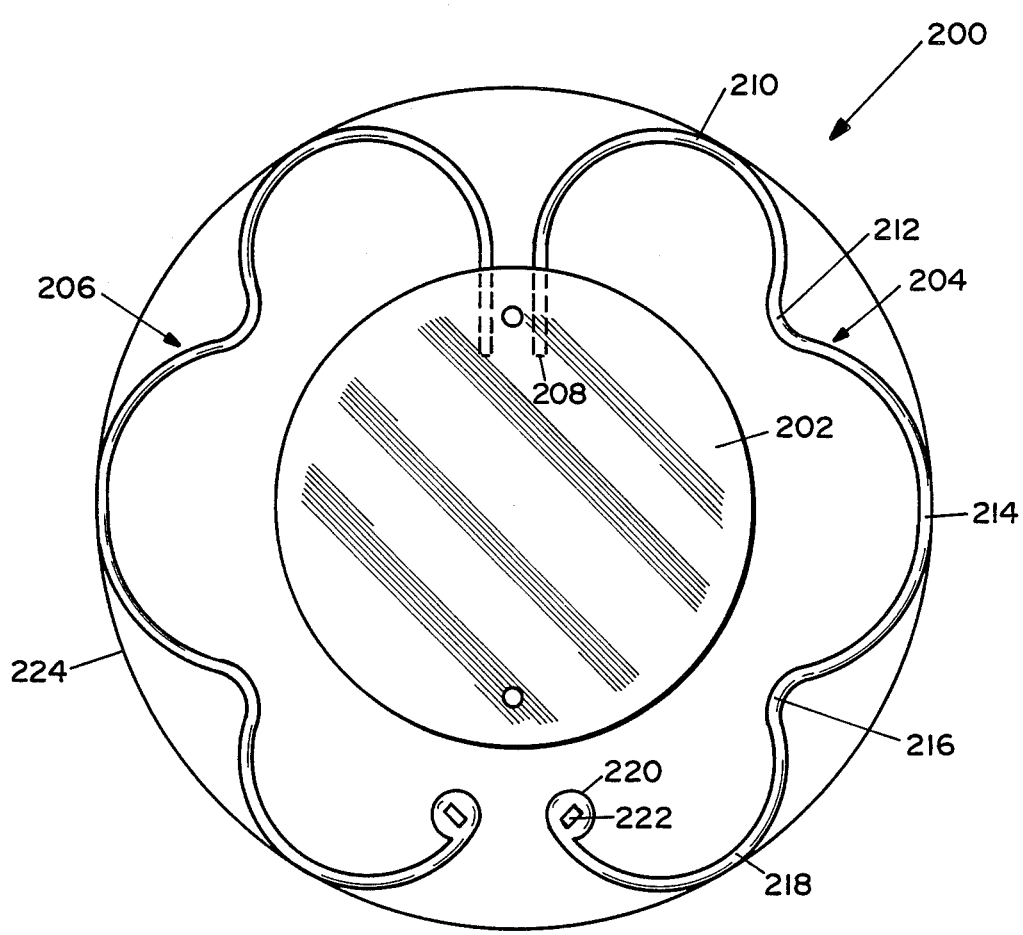
FIG. 12 illustrates a top view of a lens with three outwardly curved segments connected by two inwardly curved segments.

FIG. 12 illustrates a top view of another intraocular lens 200 including a lens optic 202 and haptic loops 204 and 206. Haptic loop 204 includes an end 208, a first outwardly curved segment 210, an inwardly curved segment 212, a second outwardly curved segment 214, another inwardly curved segment 216, another outwardly curved segment 218, a rounded end 220 and a geometrical keyhole 222. All of the segments are connected together providing a smooth flowing geometry for the haptic loop 204. Haptic loop 206 is likewise symmetrical and a mirror image of haptic loop 204. The two haptic loops 204 and 206 provide for six-point or six-area fixation within the capsular bag 224.

Figures 13, 14:
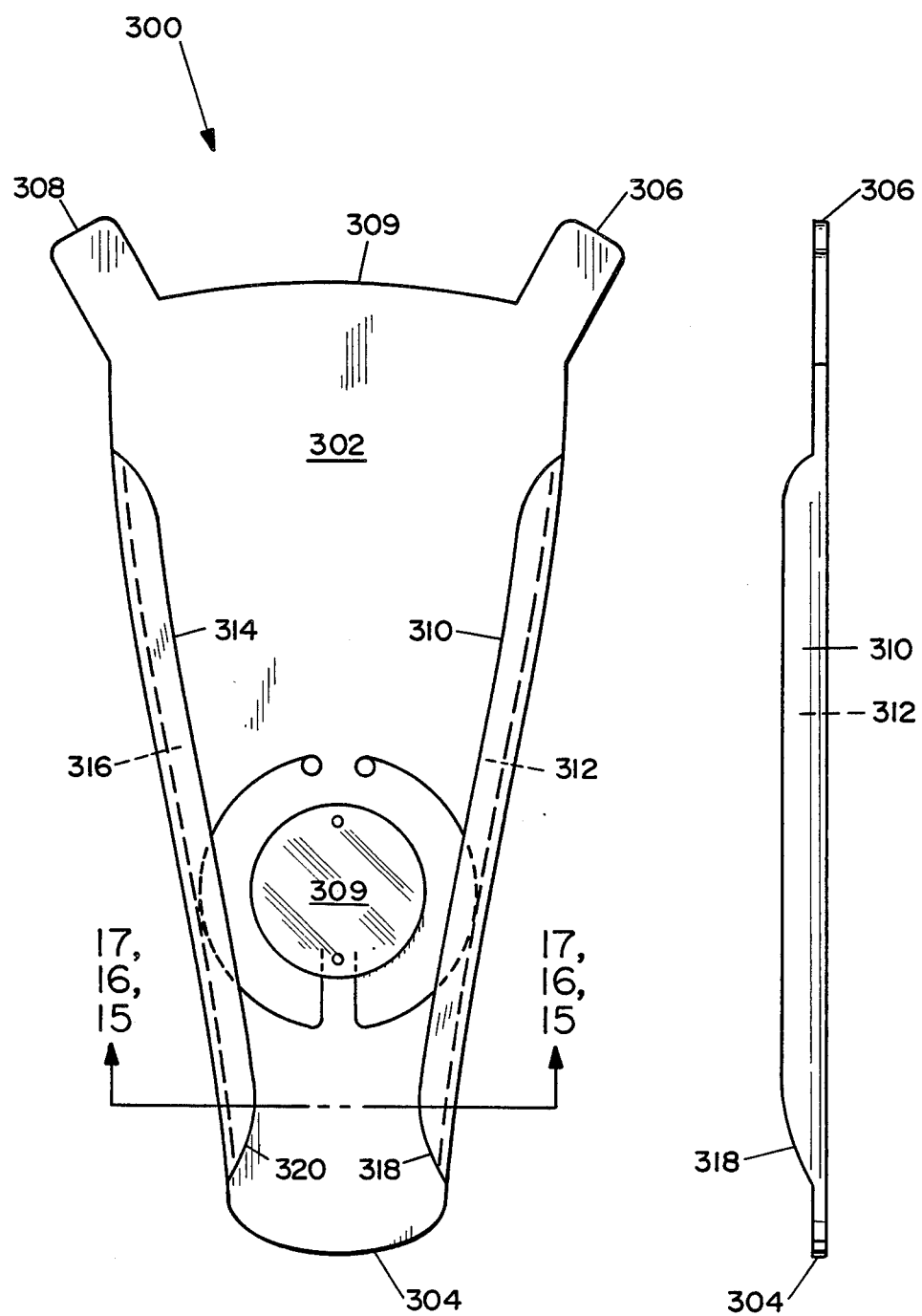
FIG. 13 illustrates a top view of an insertion slide.
FIG. 14 illustrates a side view of an insertion slide.
Figure 15:
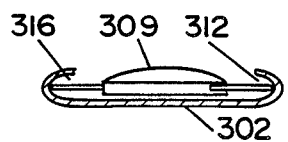
FIGS. 15 and 16 illustrate cross-sectional views of the insertion slide for different types of lens optics.
Figure 16:
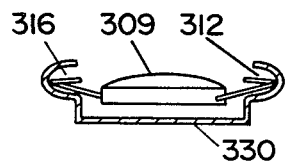
Figure 17:
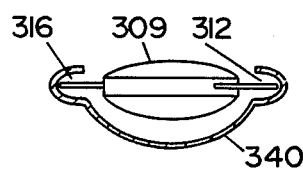

FIG. 13 illustrates a top view of an insertion slide 300 for assisting in inserting a lens into the eye. The insertion slide includes a base 302 and a rounded end 304 which is positioned through an incision in the interior capsule. Tabs 306 and 308 about end 309 provide for holding and positioning of the slide. Lips 310 and 314 provide channels 312 and 316, as illustrated in FIGS. 15-17. The base 302 of the insertion slide is of a decreasing width, providing for compressibility of the loops about the circumference of the optic, or in the alternative for angling the loops about and above and in towards the center of the optic during the compression as the lens is pushed down by a positioning tool or the like through the channels of the insertion guide. The rounded edges 318 and 320 provide for controlled release of the loops once the lens is positioned in the capsular bag or cillary sculus of the eye. Thereupon, the haptic loops will symmetrically expand as the loops are released from the channel. A lens 309, appropriately shaped, is illustrated within the insertion slide 300 with its compressed haptics engaged within channels 312 and 316.

FIG. 14 illustrates a side view of the insertion slide 300, where all numerals correspond to those elements previously described.

FIGS. 15–17 illustrate cross-sections of the insertion slide 300 taken along section lines 15—15, 16—16, and 17—17, which correspond to the previously described lens configurations. FIG. 15 corresponds to a lens with a plano surface and with planar loops. FIG. 16 is of a different cross section which includes a downwardly extending channel 330 in lieu of the planar sliding body base surface 302, as shown in FIG. 15, and is for lenses with plano surfaces with angled loops. FIG. 17 illustrates a cross-section with a curved insertion slide base 340 in lieu of the planar base 302 for bi-convex lenses or reverse optic lenses. Corresponding lens shapes are shown engaged within the slides and the haptics engaged within the corresponding channels 312 and 316.

I claim:

1. Intraocular lens comprising:
   a. lens optic; and
   b. two haptic loops, said haptic loops secured substantially adjacent to each other near a common point of securement at an edge of said lens optic and extending outwardly from said edge at an increasing angle, said haptic loops being symmetrical, double-opposing, cantilevered, compressible and mirror images of each other extending from said point of securement around and about said edge of said lens to a point substantially diametrically opposed from said point of securement for symmetrically supporting said lens in said eye, and each of said haptic loops including three semi-circular segments and two inward curved segments connecting each of said semi-circular segments together.

2. Lens of claim 1 wherein said lens optic is plano-convex.

3. Lens of claim 1 wherein said lens optic is bi-convex.

4. Lens of claim 1 wherein said lens optic is meniscus.

5. Lens of claim 1 including geometrical keyholes at the end of at least one of said haptic loops.

* * * * *